(12) United States Patent
Moons (10) Patent No.: US 9,095,318 B2
(45) Date of Patent: Aug. 4, 2015

(54) DEVICE AND METHOD FOR DETERMINING A RHEOLOGICAL PROPERTY OF MUCUS

(75) Inventor: Mathias Theodorus Maria Moons, Son en Breugel (NL)

(73) Assignee: KEN KEN B.V., Son (NL)

( * ) Notice: Subject to any disclaimer, the term of this patent is extended or adjusted under 35 U.S.C. 154(b) by 626 days.

(21) Appl. No.: 12/994,523

(22) PCT Filed: May 27, 2008

(86) PCT No.: PCT/NL2008/050318
§ 371 (c)(1),
(2), (4) Date: Jan. 6, 2011

(87) PCT Pub. No.: WO2009/145610
PCT Pub. Date: Dec. 3, 2009

(65) Prior Publication Data
US 2011/0106465 A1 May 5, 2011

(51) Int. Cl.
*G01N 11/00* (2006.01)
*G06F 19/00* (2011.01)
*A61B 10/00* (2006.01)
*G01N 11/04* (2006.01)

(52) U.S. Cl.
CPC ...... *A61B 10/0012* (2013.01); *A61B 2010/0022* (2013.01); *G01N 11/04* (2013.01); *G01N 2011/0066* (2013.01)

(58) Field of Classification Search
CPC .................. A61B 10/0012; A61B 2010/0022; G01N 11/04; G01N 2011/0066
USPC .............................. 702/50; 73/54.01; 600/551
See application file for complete search history.

(56) References Cited

U.S. PATENT DOCUMENTS

| 3,982,423 | A | | 9/1976 | Schuster |
| 4,779,627 | A | | 10/1988 | Kosasky |
| 6,149,604 | A | * | 11/2000 | Kosasky ................. 600/551 |
| 2002/0198498 | A1 | * | 12/2002 | Porat et al. ................. 604/187 |
| 2008/0208297 | A1 | * | 8/2008 | Gertner et al. ................. 607/92 |

FOREIGN PATENT DOCUMENTS

| EP | 0 835 636 A1 | 4/1998 |
| EP | 835636 A1 * | 4/1998 ............ A61B 10/00 |
| ES | 2 031 038 A6 | 11/1992 |
| FR | 2 346 718 A1 | 10/1977 |

(Continued)

OTHER PUBLICATIONS

J.M Zahm; Spinability of Respiratory Mucous, Validation of a New Apparatus 1986.*

*Primary Examiner* — Toan Le
*Assistant Examiner* — Manuel Rivera Vargas
(74) *Attorney, Agent, or Firm* — Birch, Stewart, Kolasch & Birch, LLP (57) ABSTRACT

Device and method for determining a rheological property, such as viscosity or threadability, of mucus include a housing having a circumferential surface defining an opening for receiving a quantity of the mucus, a probe extending within the housing and having a tip for contacting at least a portion of the quantity of mucus, a displacement mechanism for displacing the tip of the probe with respect to the housing, and a measurement unit for measuring a displacement of the tip of the probe. The device and method are especially suitable for determining the rheological property of mammal cervical mucus for determining female fertility.

25 Claims, 3 Drawing Sheets

(56) References Cited

FOREIGN PATENT DOCUMENTS

| JP | 10-080426 | A | 3/1998 |
| JP | 10-509364 | A | 9/1998 |
| JP | 2002-071542 | A | 3/2002 |
| JP | 3962780 | B2 | 6/2007 |
| JP | 3137107 | U | 10/2007 |
| WO | WO 96/15725 | A1 | 5/1996 |

* cited by examiner

DEVICE AND METHOD FOR DETERMINING A RHEOLOGICAL PROPERTY OF MUCUS

FIELD OF THE INVENTION

The invention relates to a device for determining a rheological property of mucus.

More specifically the invention relates to a device for determining a rheological property of cervical mucus.

BACKGROUND OF THE INVENTION

The invention is related to detecting and predicting ovulation and/or a period of fertility in a female mammal, such as a female human. Knowledge about ovulation and/or the period of fertility allows family planning in the form of avoiding pregnancy, e.g. by practising sexual abstinence or other forms of birth control during the period of fertility. Alternatively, if so desired, the probability of conceiving can be increased by practicing sexual intercourse during the female fertile period.

Ovulation and/or the period of fertility of a female can be predicted using a method referred to as natural family planning (NFP) sympto thermal method (STM). NFP/STM is a fertility awareness based (FAB) prediction method which uses as indicators for fertility a body temperature and a property of cervical mucus. NFP/STM is known in the art and will not be explained in detail here.

The average body temperature of a female human is known to change during the menstrual cycle. Commonly, the average body temperature rises by at least 0.2° C. after ovulation. Hence, monitoring the body temperature over time gives an indication of the fertility of the female.

The cervical mucus is also known to change during the menstrual cycle. During the immediate pre-ovulatory phase, for a period of one to three days, the cervical mucus is profuse and watery; the cervical mucus is most hydrated (97 to 98% water) at the time of ovulation. At other times of the menstrual cycle, the cervical mucus is less abundant, relatively dehydrated (80 to 90% water) and no longer possesses certain threadability characteristics, or in rheological terms is more viscous. Also, the cervical mucus is normally cloudy, but becomes transparent three to four days before ovulation.

It is known in the art to predict ovulation and/or the period of fertility based on body temperature and a property of the cervical mucus. One known method determines the optical transparency of the cervical mucus. It has been found, however, that determining a rheological property of the mucus allows for more accurate prediction of ovulation and/or the period of fertility.

It is known to determine a threadability of the cervical mucus by hand, by threading the mucus between the thumb and a finger by gradually increasing the distance between the thumb and the finger, e.g. until the thread of mucus breaks. This method is, however, generally regarded as messy.

Several methods and devices are known for determining a rheological property of a bodily mucus, more in particular cervical mucus for determining the phase of the menstrual cycle.

American patent specification U.S. Pat. No. 3,982,423 discloses a testing process and device wherein a sample of mucus is inserted in a thin ring shaped cavity between an inner and outer member. One member is mounted stationary, the other member is weighted to move relative to the first mentioned member when the viscosity of the mucus is relatively low and not to move when the viscosity of the mucus is relatively high. This device has the disadvantage that it gives no indication of how high the viscosity of the mucus is, but only an indication whether or not the viscosity is above or below a predetermined threshold value.

Spanish patent specification ES 2 031 038 discloses a device in the form of tweezers, wherein a sample of mucus is placed between the tips of the two legs of the tweezers. The legs are moved away from each other until a thread of mucus formed between the tips breaks. The device is provided with a scale for determining the maximum length of the thread just prior to breaking. This device has the disadvantage that the length of the thread as determined from the scale may depend largely on the skill of an operator of the device to read the scale and to maintain the legs in the relative position in which the thread broke after breaking until the scale has been read.

Further, these devices and methods have the disadvantage that they are not user-friendly and require some skill to be operated. Hence, these devices and methods are not suitable to be used by untrained persons. Especially in predicting ovulation and/or the period of fertility in women, it is strongly desirable that a woman can operate the device and/or practice the method herself, e.g. in the comfort of her own home.

BRIEF DESCRIPTION OF THE INVENTION

It is an object of the invention to provide a device for determining a rheological property of mucus which meets at least one of the above mentioned problems.

Thereto, according to the invention, a device for determining a rheological property, such as viscosity or threadability, of mucus is provided comprising a housing having a circumferential surface defining an opening for receiving a quantity of the mucus, a probe extending within the housing and having a tip for contacting at least a portion of the quantity of the mucus, a displacement mechanism for displacing the tip of the probe with respect to the housing, and a measurement unit for measuring a displacement of the tip of the probe. Hence, the device may create a thread of the mucus extending from the tip of the probe, e.g. between circumferential surface and the tip, while displacing the tip with respect to the circumferential surface. This may give an indication of a threadability of the mucus.

Preferably, the circumferential surface and the tip of the probe comprise a material and/or shape to allow adherence of the mucus thereto. Hence, the determined rheological parameters of the mucus are not, or at least insignificantly, dependent on an ability of the mucus to adhere to the rim and the tip.

Preferably, the measurement unit is arranged for detecting break of the thread of the mucus. Thus it may be determined when the thread breaks, and e.g. what the maximum elongation of the thread prior to break was. This gives a good indication of the threadability of the mucus.

In an embodiment, the measurement unit comprises an electrical power source for generating an electrical current through the thread of the mucus, and is preferably arranged for detecting break of the thread on the basis of the absence of the electrical current.

Preferably, the measurement unit is arranged for measuring a force exerted on the tip of the probe by the mucus. A measured displacement of the tip with respect to the rim and associated force exerted on the tip by the mucus give an indication of the rheological property of the mucus.

Preferably, the device is arranged for determining one of an elongation at break of the mucus, a tensile force at break of the mucus, a force-elongation profile of the mucus and a stretchability of the mucus. It has been found that these are reliable parameters from which the rheological property of the mucus can be determined.

Preferably, the housing comprises a chamber which opens into the opening, wherein a cross section of the opening is smaller than a cross section of the chamber. This aids in forming the defined thread of the mucus.

In an embodiment the housing comprises a substantially tubular portion adjacent the opening, the tubular portion being suitable for being introduced into a body cavity of a user of the device. Thus, the device can be used for determining the rheological property of the mucus in vivo.

Preferably, the probe extends substantially axially within the tubular portion of the housing. Preferably, the displacement mechanism is arranged for displacing the probe in an axial direction of the tubular portion. Hence, a particularly simple embodiment of the device may be obtained.

In an embodiment the opening comprises a cup shaped recess. The cup shaped recess may aid in gathering mucus at the opening of the housing, especially when the device is, at least partially, introduced into a body cavity comprising the mucus. Preferably, the tip of the probe extends outwardly through a hole in the bottom of the cup shaped recess. Preferably, between the inner diameter of the hole and the outer diameter of the probe at the location of the hole a gap is present having a width arranged to suck the mucus into the gap due to capillary action. Hence, the mucus is caused to properly adhere to both the tip of the probe and the cup-shaped opening of the housing.

In an embodiment the device is further provided with a temperature sensor for determining a temperature of the mucus and/or surrounding tissue. Preferably, the basal temperature, i.e. the temperature at (complete) rest, of the female body is measured. The basal temperature can e.g. be measured directly or shortly after awaking. Thus, the device is made suitable for determining whether the female mammal is fertile. Thereto, the device may comprise a processor for determining whether the female mammal is fertile based on the rheological property of the cervical mucus and/or the temperature. Preferably, the processor applies rules known from NFP/STM for determining whether or not the female is fertile. Preferably, the processor is arranged for determining an average value for the rheological property and/or the temperature on the basis of measurements performed during a previous menstrual cycle of the same female mammal.

The invention also relates to a system for determining female mammal fertility comprising a remote processing unit and a device according to the invention, further comprising a transmitter for transmitting a signal associated with a measured value of the displacement, break, force and/or temperature to the remote processing unit, wherein the remote processing unit is arranged for receiving the signal from the device, and for processing the received signal and making results of the processing knowable to a user of the system. Thus, it is possible to view data and/or perform data processing, on data obtained with the device, using the remote processing unit, such as a general purpose computer. Here the data may contain a measured value for the displacement, break, force and/or temperature, a determined value for the rheological property, such as a viscosity or threadability, and/or a processed result such as an indication of fertility or infertility.

In an embodiment the system further comprises a host-unit, such as a web server, wherein the remote processing unit is arranged for transmitting a unit signal associated with the signal received from the device to the web server, and the host-unit is arranged for receiving the unit signal, and for processing the received unit signal and making results of the processing knowable to the user of the system, e.g. via the internet. Hence, the data may be made accessible on the host-unit.

Preferably, the host-unit comprises a repository for storing data associated with unit signals received from a plurality of remote processing units. Preferably, the host-unit is arranged for performing statistical analysis on the data stored in the repository. Thus, detecting and predicting ovulation and/or a period of fertility for one specific female mammal may be performed more accurately by using statistical results, e.g. data of the same female in one or more previous menstrual cycles, or data of a plurality of females.

The invention further relates to a method for determining a rheological property of mucus, comprising applying a quantity of mucus to the opening of the housing of a device according to the invention, contacting at least a portion of the quantity of the mucus with the tip of the probe, displacing the probe in a direction away from the opening, and measuring a displacement of the tip of the probe.

Preferably, the step of applying the quantity of mucus to the opening of the housing comprises inserting the opening of the housing into a body cavity of a subject, which body cavity contains the mucus. Thus, the rheological property of the mucus can be determined in vivo.

In an embodiment the mucus is mammal cervical mucus, such as human cervical mucus. As already explained the rheological property of cervical mucus is a good indicator for fertility of the female. Although less pronounced, oral mucus is known to also be an indicator of female fertility. The rheological property of the oral mucus can be used instead of the rheological property of the cervical mucus.

The invention also relates to a method for determining and/or predicting ovulation and/or fertility in a female mammal, such as a female human, comprising determining a rheological property of mucus of the female mammal according to the invention, determining a body temperature of the female mammal, and determining and/or predicting ovulation and/or fertility on the basis of the determined rheological property and the determined body temperature. Thereto, rules of NFP/STM may be applied.

BRIEF DESCRIPTION OF THE DRAWINGS

The invention will now, by way of non-limiting example, be further elucidated referring to the accompanying drawing in which.

DETAILED DESCRIPTION

Figure 1:
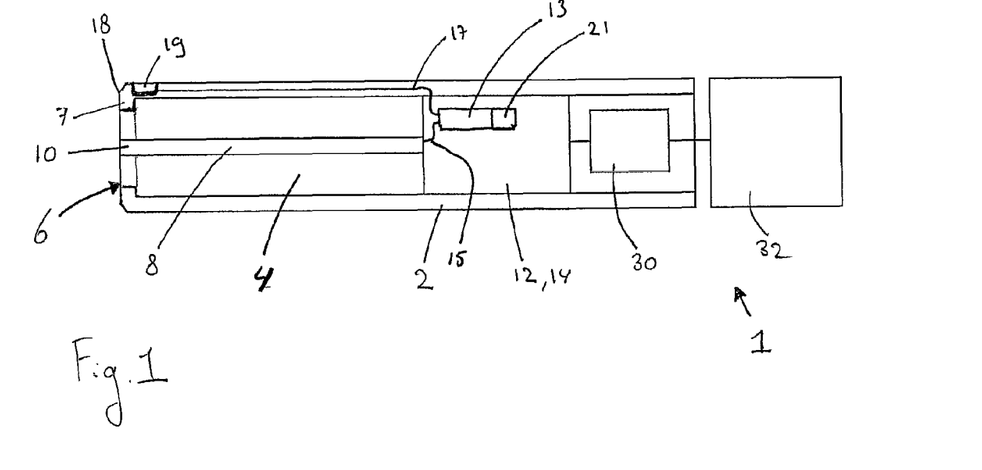
FIG. 1 shows an example of a first embodiment of a device for determining a rheological property of mucus according to the invention.

FIG. 1 shows an example of a first embodiment of a device 1 for determining a rheological property, such as viscosity or threadability, of mucus according to the invention. In this example the device 1 comprises a housing 2 having a chamber 4 with an open end 6. At the open end a circumferential surface defines an opening. In this example, a cross section of the opening formed at the open end 6 is smaller than a cross section of the chamber 4. Hence, in this example, an inwardly extending flange 7 is formed. In this example, the housing 2 is substantially tubular. In FIG. 1, the device 1 further comprises a probe 8 extending within the housing 2. In this example the probe 8 extends substantially axially within the housing 2, in a longitudinal direction of the housing 2. The probe 8 has a tip 10 which is positioned near the open end 6 of the housing 2. The device 1 further comprises a displacement mechanism 12 for displacing the probe 8 with respect to the housing 2. In this example the displacement mechanism 12 is arranged for displacing the probe 8 in a linear displacement, here axially within the housing 2.

In this example the displacement mechanism comprises a rack and gear construction wherein the rack is connected to the probe 8 and the gear is associated with an electric motor for displacing the probe. Other displacement mechanisms are however possible, such as a piston rod-like construction, a linear motor, piezoelectric displacement, a pneumatic cylinder etc.

The device 1 further comprises a measurement unit 14 provided with displacement measuring means for measuring a displacement of the probe 8. The displacement can for instance be measured using a linear or rotary digital encoder.

Figure 2A:
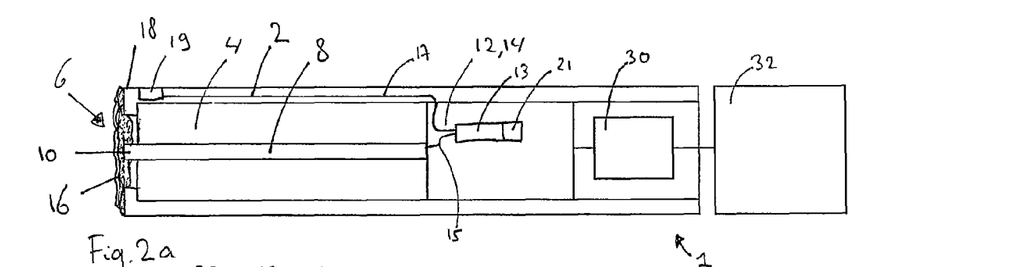
FIGS. 2a-2c show consecutive steps in the working of the device shown in FIG. 1.

The device 1 as described thus far can be used as follows. The tip 10 of the probe 8 is positioned adjacent the opening at the open end 6 of the housing 2. The open end 6 of the housing 2 is brought into contact with a quantity of mucus 16 (see FIG. 2a). The mucus 16 adheres to a circumferential rim 18 at the open end 6 of the housing 2, e.g. to the flange 7. The mucus 16 also adheres to the tip 10 of the probe 8. In this example the probe 8 is made of stainless steel and the rim 18 is made of PMMA, which prove to be suitable materials for allowing the mucus to adhere to the tip 10 and the rim 18.

Next, the displacement mechanism 12 displaces the probe 8 inwardly into the chamber 4, away from the open end 6. The mucus 16 still adheres to the rim 18 and to the tip 10. A thread 20 of the mucus 16 is formed inside the chamber 4 (see FIG. 2b). It is noted that in this example the flange 7 prevents sliding of the mucus 16 along the inner side of the wall of the chamber, during displacement of the probe 8. Thus, the flange 7 aids in forming the thread 20 of the mucus 16 extending form well defined positions, here the flange 7 of the rim 18 and the tip 10 of the probe 8.

Figure 2B:
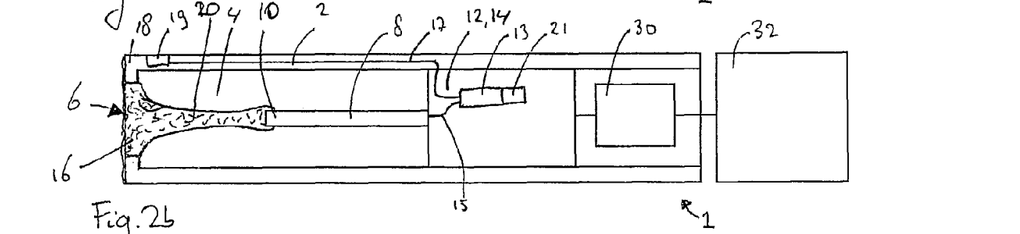

While the displacement mechanism 12 displaces the probe, the measurement unit 14 may measure the displacement of the probe 8.

In this example the measurement unit 14 further comprises break detection means for determining break of the thread 20 of mucus 16. Here, the measurement unit comprises a source 13 of electrical energy. In this example, the source 13 is a current source, although a voltage source is conceivable. The source 13 is electrically connected to the tip 10 of the probe 8, in this example via wire 15 and the probe 8. The source is also electrically connected to a contact 19 at the housing 2, in this example via wire 17. Here the contact 19 is positioned on the outside of the housing, i.e. not within the chamber 4. In this example, the contact is positioned near the rim 18.

Once the mucus 16 contacts both the tip 10 of the probe 8 and the contact 19, an electrical circuit is closed. The source 13 can cause electric current to flow through the electrical circuit, in this example via the wire 15, the probe 8, the tip 10, the mucus 16, the contact 19 and the wire 17 back to the source 13. The electrical current continues to flow during elongation of the thread 20 of the mucus 16. Once the thread 20 breaks, the current flow is interrupted. Hence, the measurement unit 14 can determine the moment of break of the thread 20 on the basis of the electrical current. The thread length at break can be determined by determining the position of the tip 10 at the moment of break.

It will be appreciated that the current preferably is small, e.g. less than or equal to 0.05 mA, in order not to cause any discomfort or danger. Preferably voltage used in the electrical circuit are small, e.g. less than or equal to 5 V, in order not to cause discomfort or danger.

The measurement unit 14 may for instance determine a threadability, a stretchability or a viscosity of the mucus 16. A threadability may e.g. be expressed as a maximum thread length at break of the thread.

In an elaborate embodiment the measurement unit 14 may further comprise force measuring means for measuring a force exerted on the probe, e.g. by the elastic contraction of the thread 20 of mucus 16. The force can for instance be measured using a strain gauge or by measuring a current flowing through the electric motor. The measurement unit 14 may then for instance determine a force-elongation profile of the mucus 16, i.e. the elastic contraction force as a function of elongation. The force exerted on the probe 8 by the elastic contraction of the thread 20 of mucus 16, e.g. as a function of elongation of the thread 20, may be used for determining the rheological property of the mucus 16. The force exerted on the probe by the elastic contraction of the thread 20 of mucus 16, e.g. as a function of elongation of the thread 20, may e.g. be used for determining the threadability, stretchability or viscosity of the mucus 16. The stretchability may e.g. be expressed as a force required for a predetermined absolute or relative elongation of the thread.

It will be appreciated that break of the thread 20 may also be detected by the force measuring means as a sudden decrease in force exerted o the probe 8.

Figure 2C:
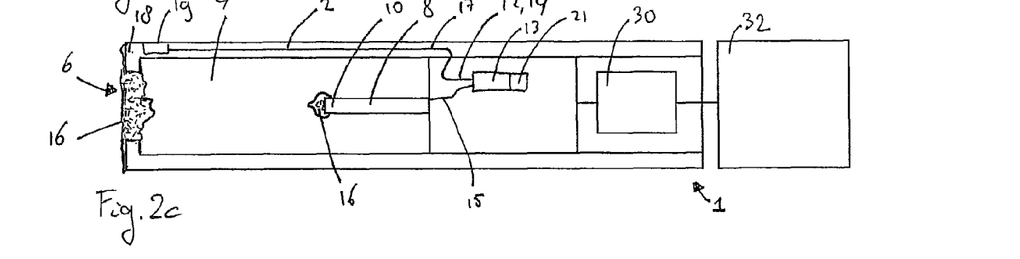

In a special embodiment, the displacement mechanism 12 displaces the probe 8 inwardly into the chamber 4, away from the open end 6 until the thread 20 of the mucus 16 breaks (see FIG. 2c). In this case, the measurement unit 14 may determine an elongation at break of the mucus 16, a tensile force at break of the mucus 16, or a force-elongation profile of the mucus 16 (i.e. force as a function of elongation). The elongation at break of the mucus 16 or the tensile force at break of the mucus 16, may be used for determining the rheological property of the mucus 16. The elongation at break of the mucus 16 or the tensile force at break of the mucus 16, may e.g. be used for determining a threadability, a stretchability or a viscosity of the mucus 16.

The device shown in FIGS. 1, 2a, 2b and 2c is further provided with a processor 30. The processor 30 is communicatively connected to the displacement mechanism 12 for controlling the displacement of the probe 8. The processor 30 is also communicatively connected to the measurement unit 14 for receiving data representative of the displacement of the probe 8 and/or data representative of the force exerted on the probe by the elastic contraction of the thread 20 of the mucus 16 and/or data representative of breaking of the thread 20. The processor may be arranged to determine the rheological property from the measured displacement at break, or from the measured displacement and force. Thereto, the processor may, e.g. in a memory, comprise a predefined algorithm to calculate the rheological property. Such algorithm may e.g. be interpolated and/or extrapolated after calibration using one or more samples of a mucus having a known value of the rheological property.

The processor 30 is in this example further communicatively connected to an indicator 32. The indicator is arranged for indicating whether or not the measurement was completed successfully. Alternatively, or additionally, the indicator is arranged for indicating information relating to the data received from the measurement unit 14, as will be further elucidated hereinbelow.

The measurement unit 14 may also be provided with a resistance measurement unit 21 arranged for measuring the electrical resistance of the mucus 16. The measurement unit 14 may use the electrical circuit associated with the electrical source 13 for determining the resistance of the mucus 16. The electrical resistance is representative of an acidity inside the vagina, and gives an indication of fertility in the female. The acidity is known to change during the menstrual cycle, and should decrease during fertile days within the menstrual cycle.

Figure 3:
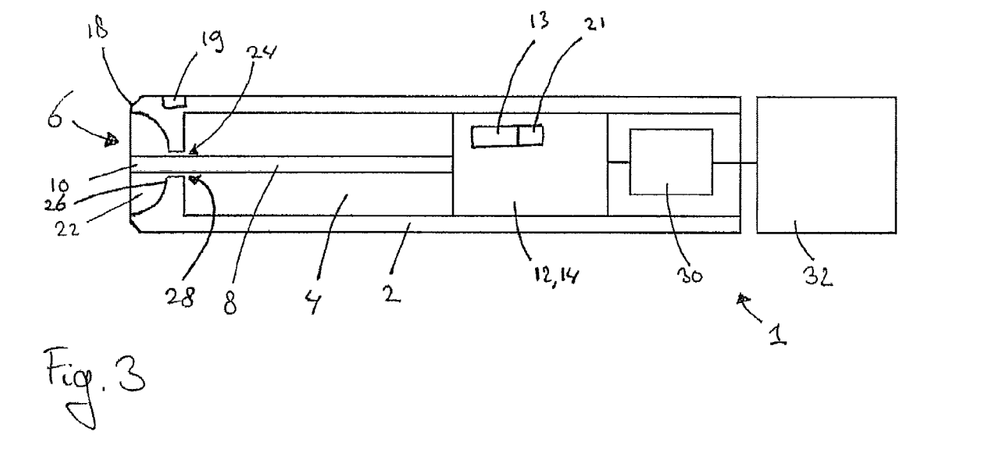
FIG. 3 shows an example of a second embodiment of the device according to the invention.

FIG. 3 shows an example of a second embodiment of the device 1 according to the invention. In the example of FIG. 3, the open end 6 comprises a cup shaped recess 22. The tip 10 of the probe 8 extends through a hole 24 in a bottom 26 of the cup shaped recess 22. In this example an inner diameter of the hole 24 is larger than an outer diameter of the probe 8 at the location of the hole 24, such that a gap 28 is present between a wall of the hole 24 and the probe 8. A width of the gap 28 is chosen such that the mucus 16 is sucked into the gap 28 due to capillary action. As an example, the width of the gap 28 may be between 0.05 and 0.3 mm. In this example, the bottom of the recess 22 forms the inwardly extending flange 7 of the circumferential rim 18.

The working of the device 1 shown in FIG. 3 is identical to the wording of the device shown in FIGS. 1, 2a, 2b and 2c. The cup shaped recess 22 provides the advantage that the quantity of mucus 16 can more easily be brought into contact with the open end 6 of the housing 2 and the tip 10 of the probe 8. Further, the gap 28 helps in having the mucus 16 properly adhere to the tip 10 of the probe 8 in order to reproducibly produce threads 20 of the mucus 16.

The device 1 for determining the rheological property of the mucus 16 according to the invention may also be used for determining the rheological property of a bodily mucus, such as cervical, oral or nasal mucus, in vivo. The device 1 may for instance be used for determining the rheological property of the mucus in a body cavity.

According to a special embodiment, the device 1 according to the invention is used for determining the rheological property of mammal cervical mucus in vivo as will be described referring to FIG. 4. In particular, the device is used for detecting fertility and/or predicting ovulation and/or a period of fertility in a female mammal. More in particular, the device is used for detecting fertility and/or predicting ovulation and/or a period of fertility in a female human being.

Figure 4:
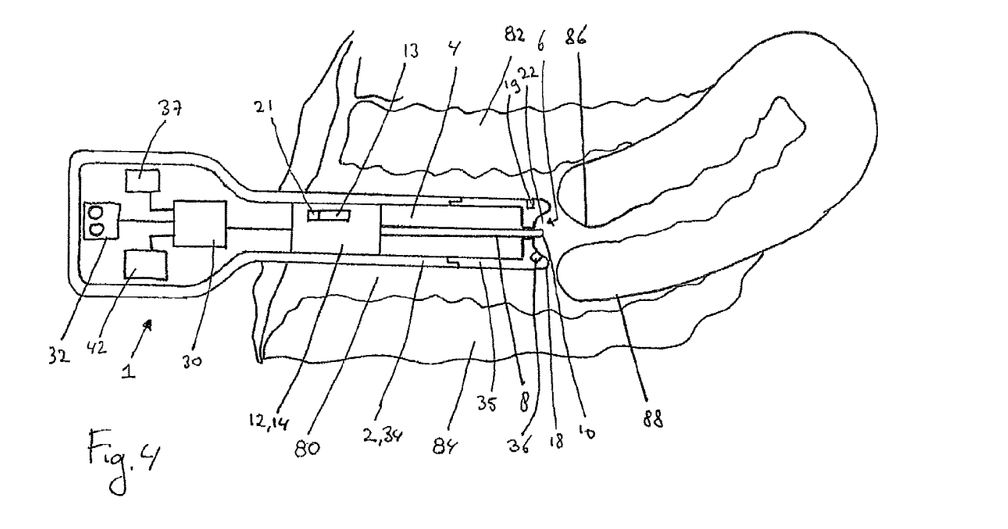
FIG. 4 shows an example of a third embodiment of the device according to the invention.

FIG. 4 shows an example of an embodiment of the device 1 according to the invention inserted into the vagina 80 of a woman. In this example a tubular portion 34 of the housing 2 is enclosed between the upper 82 and lower 84 vagina wall. In FIG. 4 a gap is drawn between the upper and lower vagina walls 82, 84 and the outside of the housing 2 for clarity. It will be appreciated that in practice the upper and lower vagina walls 82, 84 will lie in contact with the outside of the housing 2. The tubular portion 34 is preferably inserted into the vagina 80 until the circumferential rim 18 is positioned adjacent to or touching the external os 86 of the cervix 88. It will be appreciated that the tubular portion 34 and the rim 18 have rounded corners to avoid pain or injury.

In this example, a front end 35 of the tubular portion 34, comprising the rim 18 and the cup-shaped recess 22, is designed detachable from the remainder of the housing 2. This provides the advantage that the device 1 can be easily cleaned after use. Thereto, the front end 35 may be removed and the probe 8 and the inside of the chamber 4 may be rinsed with water. Additionally, or alternatively, the front end 35 and/or the probe 8 and/or the tip 10 of the probe can be constructed as a disposable. The tip 10 may e.g. be designed as a cap that connects to the remainder of the probe 8 e.g. by a snap-fit or a threaded connection. The tip 10 may have a cross section that is larger than, equal to or smaller than the remainder of the probe 8.

While inserting the tubular portion 34, the cup shaped recess 22 aids in collecting cervical mucus which has entered the rear of the vagina 80 via the external os 86. Preferably, collecting the cervical mucus at the open end 6 is performed just after awaking, when a quantity of cervical mucus has aggregated in the rear of the vagina 80. Preferably, collecting the cervical mucus at the open end 6 is performed with the woman in a lying down position. The woman may perform the procedure herself.

Once the tubular portion 34 of the device 1 is inserted into the vagina 80 as described above, the cervical mucus will contact the rim 18 and the tip 10 of the probe 8. Next, the rheological property of the mucus may be determined as described with respect to FIGS. 2a-2c. Preferably, the rheological property of the mucus is determined while the tubular portion 34 of the device remains inserted into the vagina 80. Hence, the rheological property is determined in vivo. It will be appreciated that the thread 20 of mucus 16 is formed inside the chamber 4, which in this example forms an air-filled hollow space within the vagina 80. Providing the hollow space enables forming of the thread within the vagina 80, which would otherwise be impossible.

In the example of FIG. 4 the device 1 is provided with a temperature sensor 36 for determining a temperature of the mucus and/or surrounding tissue. Hence, the device 1 is arranged to determine both the rheological property of the mucus and the body temperature. Determining the rheological property of the cervical mucus while the tubular portion 34 remains inserted into the vagina also provides the advantage that the temperature sensor remains inside the body of the woman during that time. Thus, prolonged contact between the temperature sensor and the body or bodily fluids is possible, so that the temperature can be determined more accurately.

In this example, the processor 30 is arranged for determining whether the woman is fertile based on the rheological property of the cervical mucus and the temperature. Thereto, the processor may apply the rules of NFP/STM to the measured value of the rheological property of the cervical mucus and the temperature. In this example, the processor 30 may be arranged to determine an average value for the rheological property and an average value for the temperature over a longer period of time, such as one menstrual cycle or a plurality of menstrual cycles. The processor may further be arranged to determine whether the woman is fertile or not based on a comparison of the value of the rheological property of the cervical mucus and the value of the temperature at the time the determination is made with the average value for the rheological property and the temperature. In the example of FIG. 4 the indicator 32 comprises a green and a red LED for indicating fertility or infertility, respectively. The processor 30 may be provided with a non-volatile memory for storing measured values, average values, etc.

In a more elaborate embodiment, the indicator 32 may be designed as a display device, e.g. an LCD display. The processor 30 and indicator 32 together may be arranged to display a current measurement value of the rheological property and/or the temperature, an indication of fertility, a time and/or date, etc.

In this example, the device 1 is further provided with input means 37. The input means may be designed as a button or a plurality of buttons. The input means 37 may be designed to input information into the processor 30, which information can be taken into account when determining whether the woman is fertile or not. Such information may for instance relate to illness (e.g. fever), menstruation, spotting, pain, cramps, the day within the menstrual cycle and/or the first day of the menstrual cycle (e.g. according to the NFP method the day at which menstrual bleeding starts) etc. In this example the housing 2 is totally closed and water-tight (e.g. IP class 68). The movable probe 8 may be sealed against the housing via an O-ring or quad-ring. In this example the housing is constructed of a plastics material containing an antibacterial agent.

Figure 5:
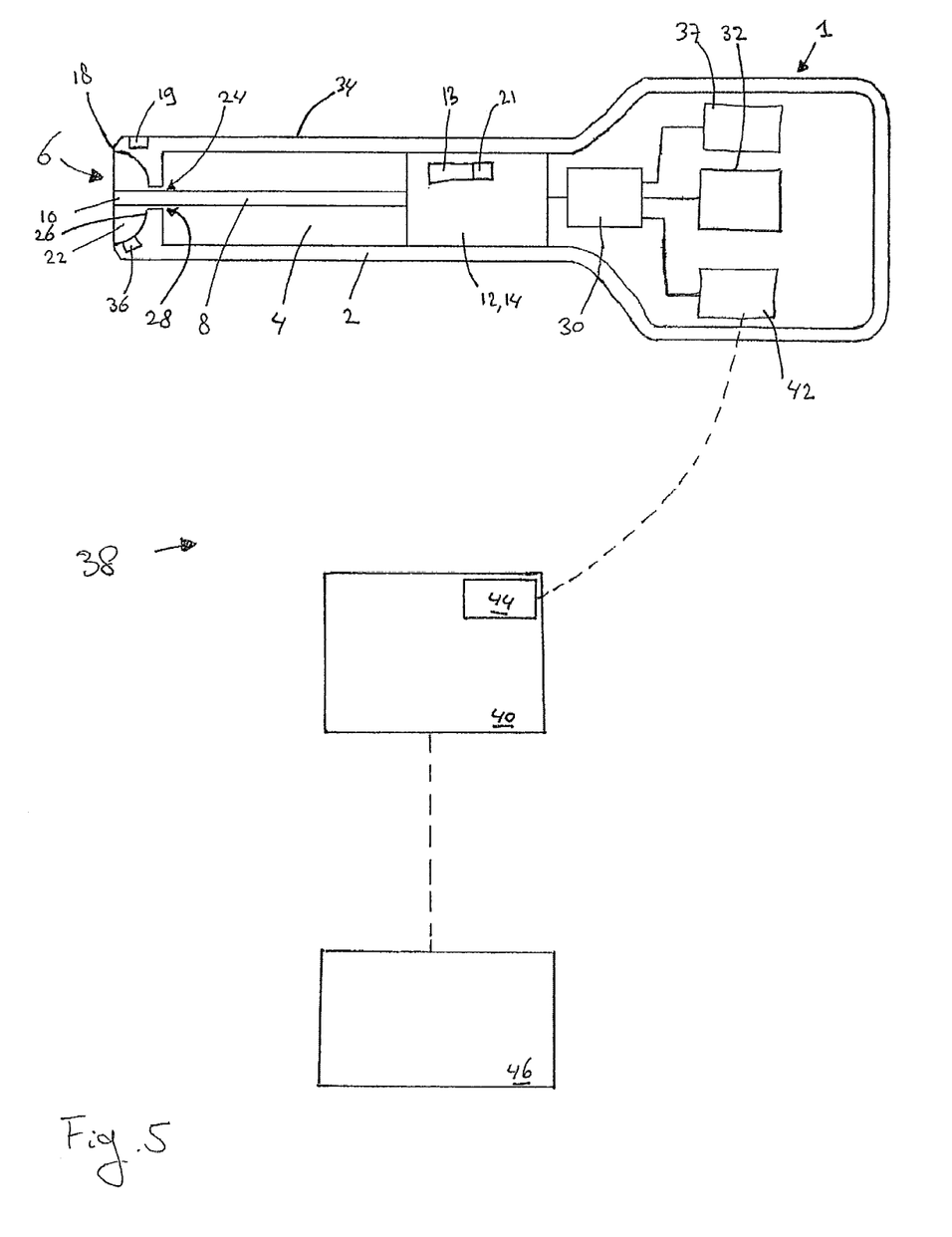
FIG. 5 shows an example of a system according to the invention.

FIG. 5 shows an example of a system 38 according to the invention. the system 38 comprises a device 1 according to the invention and a remote processing unit 40. In this example, the device 1 further comprises a transmitter 42. The transmitter 42 is communicatively connected to the processor 30, and is arranged for transmitting information associated with measurements taken by the device 1 to the remote processing unit 40. The remote processing unit is provided with a receiver 44. It will be appreciated that both the transmitter 42 and the receiver 44 may be designed as a transceiver, so that bidirectional communication is possible between the device 1 and the remote processing unit 40.

The transmitter 42 may transmit a signal representative of the measured displacement, break, force, measured value of the rheological property and/or the measured temperature to the receiver 44. Communication between the transmitter 42 and the receiver 44 may use a wireless communication protocol such as Bluetooth or ZigBee. Alternatively, or additionally, the transmitter may transmit a signal representative of data produced by the processor 30 on the basis of the measured value of the rheological property and/or temperature, such as an indication whether or not the woman is in a fertile period.

The remote processing unit 40 may be a multi purpose computer of the woman, such as a personal computer, laptop computer, personal digital assistant, or cellular telephone. The remote processing unit 40 may run software code portions for displaying the measured value of the rheological property and/or the measured temperature, and/or for displaying information deduced from said measured values.

The information which can be taken into account when determining whether the woman is fertile or not can also be inputted directly into the remote processing unit 40. This provides the advantage that the input means 37 of the device 1 may be simplified.

In a further embodiment, the remote processing unit 40 is communicatively connected to a web server 46. The remote processing unit 40 transmits a signal representative of the measured displacement, break, force, the measured value of the rheological property and/or the measured temperature to the web server 46. The data enclosed in the signal is stored and processed at the web server 46. The woman may now view the measurement results at the web server, e.g. by logging in using an account name and password, e.g. via the internet using a web browser on her computer. Optionally the woman may set accounts and privileges for others, such as a general practitioner, gynaecologist and/or husband, authorised to look into the woman's data at the web server.

The remote processing unit 40 and/or the web server 46 may present the measured values to the woman in a cycle chart. The cycle chart is known per se for use in the field of female fertility and NFP/STM methods. According to an aspect of the invention, the device 1, remote processing unit 40 or web server 46 may, completely or partly, fill in the cycle chart, based on measured values, deduced values and/or additional information entered using the input means, remote processing unit 40 and/or web-server 46. Preferably, it remains possible to fill in or amend the cycle chart manually. Preferably, a log is kept of who amended the chart and optionally when.

Since the temperature and the rheological property of the cervical mucus are known to vary during the menstrual cycle, it is advantageous if the processor 30, remote processing unit 40 and/or web-server 46 has knowledge about the day within the menstrual cycle. After e.g. inputting the first cycle day manually by using the input means 37, the processor 30, remote processing unit 40 and/or web-server 46 determines, e.g. all, other days within the menstrual cycle based on measurements of the clocktime duration of one or more previous menstrual cycles and on the measurements of the rheological property of the cervical mucus and/or the temperature in the one or more previous menstrual cycles. Hence, the processor 30, remote processing unit 40 and/or web-server 46 may compensate for systematic deviations the woman has from a standard menstrual cycle of 28 days, or systematic deviations from e.g. ovulation within the menstrual cycle. The processor 30, remote processing unit 40 and/or web-server 46 may also determine from measurements of the rheological property of the cervical mucus and the temperature in the one or more previous menstrual cycles the expected starting point and/or duration of the period of fertility of the woman in relation to certain measured deviations in the rheological property of the mucus and/or the temperature during a present menstrual cycle. Hence, determination of fertility and/or prediction of ovulation and/or the period of fertility can be performed more accurately. Also, in this way non-systematic deviation from the normal menstrual cycle for the specific woman may be detected by the processor 30, remote processing unit 40 and/or web-server 46, giving an indication of the fertility of the woman.

Preferably, the web server comprises a data-base in which are stored measured values of the rheological property and/or the measured temperature of a plurality of women for a plurality of days, preferably a plurality of menstrual cycles. Hence, the web server has (e.g. anonymous) access to a large quantity of measured values. Thus, statistical analysis can be performed on the contents of the data-base. The web server may be arranged to analyse each measured value when it is entered into the database. Based on the statistical analysis the web server can accurately determine whether a measured value is within a natural variation or has an alarming value. In the latter case the web server may issue a message to the woman concerned, possibly suggesting medical consultation or be aware of her menopause.

The web server may also be arranged to transmit measured values and/or information deduced from said values to the remote processing unit 40. Thus, it is for instance possible that determining whether or not the woman is fertile is performed at the web server 46, while displaying the results of said determining is performed at the remote processing unit 40. It will be appreciated that it is also possible that the web server receives measured values from the remote processing unit 40, such as a personal computer, and transmits information deduced from said values to a further remote processing unit, such as a cellular telephone, e.g. in the form of an SMS message. The web server 46 may thus initiate transmission of a message stating whether or not the woman is in a fertile period.

The web server 46 may also be arranged to transmit a software and/or firmware upgrade to the remote processing unit 40 and/or to the device 1. In this way, functioning of the device 1 or system 38 may be adjusted if so desired.

In the foregoing specification, the invention has been described with reference to specific examples of embodiments of the invention. It will, however, be evident that various modifications and changes may be made therein without departing from the broader spirit and scope of the invention as set forth in the appended claims.

Although in the description reference is made to cervical mucus, it will be appreciated that the device according to the invention may be used for determining the rheological property of any mucus, such as cervical, oral or nasal mucus.

In the examples the tip of the probe is displaced in a linear motion. It is also possible that the tip of the probe is displaced along a curved path, e.g. pivoting about an axis.

In the examples, the thread of the mucus is created between the tip of the probe and the circumferential rim. It will be appreciated that it I also possible to create the thread between the tip and the tissue of the vagina or another part of the device that is stationary with respect to the housing. It is also possible to create the thread between the tip of the probe and a member that also moves with respect to the housing at a rate and/or in a direction that differs from the rate and/or direction in which the tip of the probe moves. The thread may e.g. be created between two probes. In general it applies that the thread is created extending from the tip of the probe.

In FIG. 4 the device comprises the detachable front end 35. It will be appreciated that the device in the embodiments shown in FIGS. 1-3 and 5 may also be provided with the detachable front end.

In the examples, the remote processing unit is a multi purpose computer. The remote processing unit may also be designed as a docking station for charging an internal battery of the device and for forming a communication port between the device and the web server. It is not necessary that the remote processing unit actually alters information content of the signals received from the device and/or displays information contained in said signals.

However, other modifications, variations and alternatives are also possible. The specifications, drawings and examples are, accordingly, to be regarded in an illustrative rather than in a restrictive sense.

In the claims, any reference signs placed between parentheses shall not be construed as limiting the claim. The word 'comprising' does not exclude the presence of other features or steps then those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to advantage.

The invention claimed is:

1. Device for determining a rheological property, such as viscosity or threadability, of mucus comprising:
    a housing having a circumferential surface defining an opening for receiving a quantity of the mucus, wherein the housing comprises a substantially tubular portion adjacent the opening for introducing the tubular portion into a body cavity of a user of the device,
    a probe extending within the tubular portion of the housing and having a tip for contacting at least a portion of the quantity of mucus,
    a displacement mechanism for displacing the tip of the probe in a direction away from the opening with respect to the housing, wherein the device is arranged for creating a thread of the mucus extending from the tip of the probe to the circumferential surface defining the opening while displacing the tip, and
    a measurement unit for measuring a displacement of the tip of the probe in the direction away from the opening, wherein the measurement unit comprises an electrical power source for generating an electrical current through the thread of the mucus, wherein the measurement unit is arranged for detecting break of the thread on the basis of the absence of the electrical current.

2. Device according to claim 1, wherein the device comprises a transmitter for transmitting a signal associated with a measured value of the displacement and/or break to a remote processing unit.

3. System for determining female mammal fertility comprising a device according to claim 2 and a remote processing unit,
    wherein the remote processing unit is arranged for receiving the signal from the device, and for processing the received signal and making results of the processing knowable to a user of the system.

4. System according to claim 3, further comprising a host-unit, wherein the remote processing unit is arranged for transmitting a unit signal associated with the signal received from the device to the host-unit, and the host-unit is arranged for receiving the unit signal, and for processing the received unit signal and making results of the processing knowable to the user of the system, e.g. via the internet.

5. System according to claim 4, wherein the host-unit comprises a repository for storing data associated with unit signals received from a plurality of remote processing units.

6. System according to claim 5, wherein the host-unit is arranged for performing statistical analysis on the data stored in the repository.

7. Device according to claim 1, wherein the opening comprises a cup shaped recess.

8. Device according to claim 7, wherein the tip of the probe extends outwardly through a hole in the bottom of the cup shaped recess.

9. Device according to claim 8, wherein between the inner diameter of the hole and the outer diameter of the probe at the location of the hole a gap is present having a width arranged to suck the mucus into the gap due to capillary action.

10. Device according to claim 1, wherein the measurement unit is arranged for measuring a force exerted on the tip of the probe by the mucus.

11. Device according to claim 1, wherein the circumferential surface and the tip of the probe comprise a material and/or shape to allow adherence of the mucus thereto.

12. Device according to claim 1, wherein the device is arranged for determining one of an elongation at break of the mucus, a tensile force at break of the mucus, a force-elongation profile of the mucus and a stretchability of the mucus.

13. Device according to claim 1, wherein the housing comprises a chamber which opens into the opening, wherein a cross section of the opening is smaller than a cross section of the chamber.

14. Device according to claim 1, wherein the probe extend substantially axially within the tubular portion of the housing.

15. Device according to claim 1, wherein the displacement mechanism is arranged for displacing the probe in an axial direction of the tubular portion.

16. Device according to claim 1, wherein the device is further provided with a temperature sensor for determining a temperature of the mucus and/or surrounding tissue.

17. Device according to claim 1, wherein the device comprises a processor for determining whether a female mammal is fertile based on the rheological property of the cervical mucus and/or the temperature.

18. Device according to claim 1, wherein the measurement unit is further configured to measure a force exerted on the tip of the probe by the mucus and/or a temperature of the mucus, and the transmitter is further arranged for transmitting a signal associated with a measured value of the force and/or temperature to a remote processing unit.

19. Method for determining a rheological property, such as viscosity or threadability, of mucus, the method comprising the steps of:
    providing a device comprising:
        a housing having a circumferential surface defining an opening for receiving a quantity of the mucus, wherein the housing comprises a substantially tubular portion adjacent the opening for introducing the tubular portion into a body cavity of a user of the device,
        a probe extending within the tubular portion of the housing and having a tip for contacting at least a portion of the quantity of mucus,
        a displacement mechanism for displacing the tip of the probe in a direction away from the opening with respect to the housing, wherein the device is arranged for creating a thread of the mucus extending from the tip of the probe to the circumferential surface defining the opening while displacing the tip, and
        a measurement unit for measuring a displacement of the tip of the probe in the direction away from the opening, wherein the measurement unit comprises an electrical power source for generating an electrical current through the thread of the mucus, wherein the measurement unit is arranged for detecting break of the thread on the basis of the absence of the electrical current,
    applying a quantity of mucus to the opening of the housing of the device,
    contacting at least a portion of the quantity of the mucus with the tip of the probe,
    displacing the probe in a direction away from the opening,
    creating the thread of the mucus extending between a circumferential surface defining the opening and the tip of the probe while displacing the tip,
    measuring a displacement of the tip of the probe in the direction away from the opening,
    detecting break of the thread of the mucus on the basis of the absence of the electrical current through the thread of the mucus, and
    determining an elongation of the mucus at break on the basis of the displacement of the tip of the probe.

20. Method according to claim 19, wherein the mucus is female mammal cervical mucus.

21. Method according to claim 20, wherein the mucus is female human cervical mucus.

22. Method for determining and/or predicting ovulation and/or a period of fertility in a female mammal, comprising
    determining a rheological property of mucus of the female mammal according to claim 19,
    determining a body temperature of the female mammal, and
    determining and/or predicting ovulation and/or fertility on the basis of the determined
    rheological property and the determined body temperature.

23. Method according to claim 22, wherein the female mammal is a female human.

24. Method according to claim 19, comprising measuring a force exerted on the tip of the probe by the mucus.

25. Method according to claim 19, wherein the step of applying the quantity of mucus to the opening of the housing comprises
    inserting the opening of the housing into a body cavity of a subject, which body cavity contains the mucus.

* * * * *